US012805968B2

(12) United States Patent
Hueber et al.

(10) Patent No.: US 12,805,968 B2
(45) Date of Patent: Nov. 24, 2026

(54) SURGICAL INFORMATION SYSTEM AND METHOD OF OPERATING THE SAME, METHOD OF PROVIDING A SEQUENCE OF VIEWS ON A 3D MODEL

(71) Applicant: OLYMPUS Winter & Ibe GmbH, Hamburg (DE)

(72) Inventors: Mathias Hueber, Hamburg (DE); Sascha Jaskola, Hamburg (DE); Jan Niebuhr, Kiel (DE); Per Suppa, Hamburg (DE); Jan Alexander Thies, Verden (DE); Juri Sverdlov, Hamburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 82 days.

(21) Appl. No.: 19/078,688

(22) Filed: Mar. 13, 2025

(65) Prior Publication Data

US 2025/0302574 A1 Oct. 2, 2025

(30) Foreign Application Priority Data

Mar. 27, 2024 (EP) .................................... 24166973

(51) Int. Cl.
*G06T 19/20* (2011.01)
*A61B 90/00* (2016.01)
(Continued)

(52) U.S. Cl.
CPC ............ *A61B 90/361* (2016.02); *G06T 15/20* (2013.01); *G06T 19/20* (2013.01); *G16H 50/20* (2018.01);
(Continued)

(58) Field of Classification Search
None
See application file for complete search history.

(56) References Cited

U.S. PATENT DOCUMENTS

2017/0312031 A1 11/2017 Amanatullah et al.
2023/0301719 A1 9/2023 Murphy
(Continued)

FOREIGN PATENT DOCUMENTS

JP 2020533681 A 11/2020
KR 20210104190 A 8/2021
WO WO-2019051080 A1 * 3/2019 ............. A61B 34/10

OTHER PUBLICATIONS

Maxime Peralta et al. "Machine learning in deep brain stimulation: A systematic review", Artificial Intelligence in Medicine, XP086874634, vol. 122, Oct. 18, 2021.

*Primary Examiner* — Robert J Craddock
(74) *Attorney, Agent, or Firm* — Scully, Scott, Murphy & Presser, P.C.

(57) ABSTRACT

A surgical information system having: a first processing device in a working area configured to: provide and reproduce a 3D model of a body part; receive instructions defining a sequence of views on the 3D model in that every view defines an orientation of the 3D model and the sequence defines a chronological order of the views on the 3D model; store the sequence of views together with the 3D model; and transmit the sequence of views and the 3D model to the second processing device located in the clean area; and a second processing device in a clean area configured to reproduce the sequence of views transmitted by the first processing device on a displaying device.

20 Claims, 4 Drawing Sheets

(51) Int. Cl.
*G06T 15/20* (2011.01)
*G16H 50/20* (2018.01)

(52) U.S. Cl.
CPC .................... *A61B 2090/367* (2016.02); *A61B 2090/373* (2016.02); *G06T 2200/24* (2013.01); *G06T 2210/41* (2013.01); *G06T 2219/2016* (2013.01)

(56) References Cited

U.S. PATENT DOCUMENTS

| | | | | |
|---|---|---|---|---|
| 2024/0423582 | A1* | 12/2024 | Bharat .................. | A61B 8/085 |
| 2025/0174344 | A1* | 5/2025 | Cowperthwait ....... | A61B 90/98 |

* cited by examiner

SURGICAL INFORMATION SYSTEM AND METHOD OF OPERATING THE SAME, METHOD OF PROVIDING A SEQUENCE OF VIEWS ON A 3D MODEL

CROSS-REFERENCE TO RELATED APPLICATION

This application claims priority under 35 U.S.C. § 119 to European Patent Application No. EP 24 166 973.8, filed on Mar. 27, 2024. The entire disclosure of European Patent Application No. EP 24 166 973.8 is incorporated by this reference.

BACKGROUND

The invention relates to a surgical information system for providing a sequence of views on a 3D model of a body part. Furthermore, the invention relates to a method of providing a sequence of views on a 3D model of a body part. The invention also relates to a method of operating a surgical information system for providing a sequence of views on a 3D model of a body part. The invention also relates to a non-transitory computer-readable storage medium storing instructions for causing a surgical information system to provide a sequence of view on a 3D model of a body part.

In a surgical environment, for example in a hospital, the surgeon is often provided with an individual 3D model of a part of the patient's body in preparation for a surgical procedure. The body part is, for example, an organ or an area comprising several organs, on or in which a surgical procedure is planned. The surgeon is provided with the relevant data a few days before the actual surgical procedure. On this basis, the surgeon considers and plans an individual schedule for the surgical procedure. This differs from patient to patient. The reason for this are, on the one hand, the individuality of the case (e.g. the location, number or size of tumors or other malignant tissue intended for removal), as well as the individuality of the patient's anatomy. For example, the course of veins or arteries within the parenchyma of the liver or the general state of health differs from patient to patient.

The surgeon memorizes the individual steps in his head or writes them down on a sheet of paper while planning the procedure. This traditional approach offers only a limited or no possibility of documenting the schedule. Furthermore, there is only a very limited possibility of displaying the carefully thought-out schedule in a surgical environment. The ability to share the schedule with the other people involved in the procedure is also very limited.

It is an object of the subject application to overcome the drawbacks in the prior art.

SUMMARY

The object is solved by a surgical information system for providing of a sequence of views on a 3D model (three-dimensional model) of a body part in a surgical environment having a working area and a clean area, the system comprising a first processing device located in the working area and a second processing device located in a clean area, wherein the first processing device is configured to a) provide and reproduce a 3D-model of a body part, b) receive instructions defining a sequence of views on the 3D model in that every view defines an orientation of the 3D model and the sequence defines a chronological order of the views on the 3D-model, c) store the sequence of views together with the 3D model, and d) transmit the sequence of views and the 3D model to the second processing device located in the clean area, the second processing device is configured to e) reproduce the sequence of views on a displaying device forming part of the second processing device.

The surgical information system advantageously provides the possibility to transfer planning information relative to for example a surgical procedure from a working area to a clean area. The working area is for example an area in a surgical facility, for example a hospital, which is not necessarily sterile. Taking any item, for example a notebook or a piece of paper, from this area so a clean area, is generally undesirable. The clean area is in particular a sterile area, for example an operating room. With the surgical information system, it is not necessary to take any item from the working area to the clean area. This enhances the hygienic level. Furthermore, the full information, based on which the planning was conducted, which means the 3D model of the body part and the corresponding views, can be transferred to the clean area. The sequence of views can serve as a procedural planning for a surgical procedure. The sequence is stored on the first and second processing unit. Hence, it is possible to provide a documentation of the planning. Storage of the sequence reliefs the person concerned with the procedure from memorizing the individual steps of the planning. This is in particularly advantageous because many planning is conducted several days in advance of the actual procedure.

The first processing device and the second processing device are for example computers, workstations or other suitable devices. Preferably, the first processing device is provided with a screen or a monitor for reproducing the 3D-model of a body part.

According to an option, the surgical information system advantageously allows switching between the views. For example, the views can be switched in backward or forward direction. Optionally, individual views can be skipped.

According to an embodiment of the subject application, the surgical information system is further enhanced in that the 3D model comprises a plurality of sub-parts forming the body part and the instructions received in feature b) comprise instructions on a transparency value of at least one sub-part, wherein the first processing device is further configured to additionally store the transparency value of the sub-part(s) in the sequence of views in feature c) and to transmit said sequence of views according to feature d) and the second processing device is further configured to reproduce said sequence of views according to feature e).

Advantageously, the view does not only define the orientation of the 3D model in for example a Cartesian coordinate system, but also defines a transparency value for at least one sub-part of the 3D model. The transparency value is for example the opacity of the sub-part. Additionally setting a transparency value of at least one sub-part can be advantageous because in many configurations, structures or parts of for example an organ or complex tissue are hidden by other parts of the organ or tissue. However, detailed knowledge of the spatial configuration of all structures, which means visible and hidden structures, can be crucial for success of the treatment. Hence, setting for example an opacity of a sub-part to a value that reveals the underlying structures of another sub-part can be very helpful.

According to still another embodiment, there is a surgical information system that is further enhanced in that the first processing device is further configured to provide a plurality of virtual camera positions each defining a direction of view on the 3D model, and to receive instructions according to feature b), which comprise instructions on at least one selected virtual camera position and to additionally store the selected virtual camera position(s) in the sequence of views according to feature c) and to transmit said sequence of views according to feature d), wherein the second processing device is further configured to d1) receive instructions indicative of a selected virtual camera and to reproduce the sequence of views from the direction of view on the 3D model as defined by the selected virtual camera according to feature e).

Defining a plurality of virtual cameras adds a further degree of freedom to the display of the 3D model. The user can tailor or supplement the sequence of views by adding several viewing directions. This further enhances the procedural planning, which can be conducted with that surgical information system.

According to still another embodiment, this surgical information system can be further enhanced in that the instructions on the at least one selected virtual camera position comprise a selection of a default virtual camera position, wherein the first processing device is further configured to additionally store the default virtual camera position in the sequence of views according to feature c) and to transmit said sequence of views according to feature d), wherein the second processing device is further configured to d2) receive an instruction indicative of a selection of the default virtual camera and to reproduce at least one view of the sequence of views from the direction of view on the 3D model as defined by the selected default virtual camera according to feature e).

The definition of a default virtual camera simplifies the handling of the surgical information system. In the unexpected event that the user should be somehow confused or overstrained by the number of possible views, the option to fall back to the default view will very quickly clarify the situation. This option will help the used to quickly gain control of the situation.

The surgical information system can be further enhanced in that the first processing device is further configured to a0) receive input data indicative of data patient data, instrument data and/or data relative of preferences of a surgeon, perform a classification of views using a computer-based clinical decision support system (CDSS) implemented in the first processing device, base the classification on the received input data, wherein the first processing device is configured to perform the classification of views in that it:

receives a plurality of views through an input interface of the CDSS as an input feature of an artificial intelligence (AI) model, performs an inference operation by a processor, in which the plurality of views is applied to the AI model to generate the classification of views, communicates the classification of views through a user interface (UI) of the first processing device as a preselection of views, based on which the definition of the sequence of views on the 3D model is performed.

The application of a computer-based clinical decision support system (CDSS) opens the possibility to perform a preselection of views using an artificial intelligence model. The artificial intelligence model can be pre-trained, for example on the basis of data relating to similar surgical procedures. The artificial intelligence model can hence suggest a collection of views which were helpful in previous cases. This preselection can help or assist during manual selection of the views defining the sequence of views serving as procedural planning The surgical information system can be further enhanced in that the first processing device is configured to receive instructions according to feature b), which comprise instructions on a selection of at least one view as a milestone-view in the sequence of views, additionally store the milestone-view(s) in the sequence of views according to feature c), transmit said sequence of views to the second processing device according to feature d), wherein the second processing device is further configured to d3) receive instructions indicative of a selection of a milestone-view and to reproduce the selected milestone-view according to feature e).

In many surgical procedures, there are milestones, at which certain standard procedures are performed. The surgical information system according to the embodiment allows to establish a link between a view and such a milestone by defining a milestone-view. The surgeon is automatically prompted to the milestone that was identified during the planning of the procedure.

According to still another embodiment, the surgical information system can be enhanced in that the second processing device is further configured to receive a signal from a surgical instrument coupled to the second processing device, the signal being indicative of a milestone action or use of the surgical instrument, wherein signal triggers the selection of the milestone-view as an instruction indicative of a selection of a milestone-view according to feature d3).

Advantageously, the surgical information system is linked or coupled to a surgical instrument and receives a trigger signal indicating that a certain milestone in the procedure has been reached. For example, this can be the operation of an HF-generator supplying high voltage to a surgical tool. This tool is typically used at the end of a certain sequence of surgical steps, for example after removal of malicious tissue. By finishing this sequence of steps, a certain milestone is reached and a surgical standard procedure has to be performed. The system will automatically prompt the user to the requirement to perform the standard procedure.

The object is further solved by a method of providing a sequence of views on a 3D model of a body part in a surgical environment, the surgical environment comprising a working area and a clean area, the method comprising the steps of:

a) providing and reproducing a 3D model of a body part on a first processing device located in the working area, b) receiving instructions at the first processing device, the instructions defining a sequence of views on the 3D model in that every view defines an orientation of the 3D model and the sequence defines a chronological order of the views on the 3D model, c) storing the sequence of views together with the 3D model, d) transmitting the sequence of views and the 3D model to a second processing device located in the clean area, e) reproducing the sequence of views on a displaying device forming part of the second processing device.

According to an option, the method comprises the step of switching between views, for example in backward or forward direction. The method can also comprise the optional step of skipping one or more views.

Furthermore, same or similar advantages, which have been mentioned with respect to the surgical information system apply to the method of providing a sequence of views on the 3D model of a body part in a surgical environment in a same or similar way. Therefore, these advantages and options for enhancement of the method shall not be repeated.

According to an embodiment, the method is further enhanced in that the 3D model in step a) comprises a plurality of sub-parts forming the body part and the instructions received in step b) comprise instructions on a transparency value of at least one sub-part, wherein the transparency value of the sub-part(s) is additionally stored in the sequence of views in step c) and said sequence of views is transmitted in step d) and reproduced in step e).

In still another embodiment of the subject application, the method further comprising the step a1) of providing a plurality of virtual camera positions each defining a direction of view on the 3D model, wherein the instructions received in step b) comprise instructions on at least one selected virtual camera position and the selected virtual camera position(s) is/are additionally stored in the sequence of views in step c) and said sequence of views is transmitted in step d), the method further comprising the step d1) of receiving instructions indicative of a selected virtual camera at the second processing device and step e) comprises reproducing the sequence of views from the direction of view on the 3D model as defined by the selected virtual camera.

According to an option, the method comprises the step of switching between virtual cameras during reproduction of the sequence.

The method can be further enhanced in that the instructions on the at least one selected virtual camera position comprise a selection of a default virtual camera position, which is additionally stored in the sequence of views in step c) and said sequence of views is transmitted in step d), wherein the method further comprising the step d2) of receiving an instruction indicative of a selection of the default virtual camera at the second processing device and step e) comprises reproducing at least one view of the sequence of views from the direction of view on the 3D model as defined by the selected default virtual camera.

In another embodiment, the method further comprising the step a0) of performing a classification of views using a computer-based clinical decision support system (CDSS) implemented in the first processing device, the classification being based on input data received in the further step a0), said instructions being indicative of data patient data, instrument data and/or data relative of preferences of a surgeon, the step of performing the classification of views comprising:

receiving a plurality of views through an input interface of the CDSS as an input feature of an artificial intelligence (AI) model, performing an inference operation by a processor, in which the plurality of views is applied to the AI model to generate the classification of views, and communicating the classification of views through a user interface (UI) of the first processing device as a preselection of views, based on which the step b) of defining the sequence of views on the 3D model is performed.

The method can be further enhanced in that the instructions received in step b) comprise instructions on a selection of at least one view as a milestone-view in the sequence of views, and wherein the milestone-view(s) is/are additionally stored in the sequence of views in step c) and said sequence of views is transmitted in step d) to the second processing device, and the method further comprising the step d3) of receiving instructions indicative of a selection of a milestone-view and step e) comprises reproducing the selected milestone-view.

In still another embodiment, the method further comprising receiving of a signal from a surgical instrument coupled to the second processing device, the signal being indicative of a milestone action or use of the surgical instrument, wherein the signal triggers the selection of the milestone-view in step d3).

The object is further solved by a method of operating a surgical information system for providing of a sequence of views on a 3D model of a body part in a surgical environment having a working area and a clean area, the system comprising a first processing device located in the working area and a second processing device located in a clean area, the method comprising the steps of:

a) providing and reproducing a 3D model of a body part on the first processing device, b) receiving instructions at the first processing device, the instructions defining a sequence of views on the 3D model in that every view defines an orientation of the 3D model and the sequence defines a chronological order of the views on the 3D model, c) storing the sequence of views together with the 3D model in the first processing device, d) transmitting the sequence of views and the 3D model from the first to the second processing device, e) reproducing the sequence of views on a displaying device forming part of the second processing device.

Same or similar advantages, which have been mentioned with respect to the surgical information system and with respect to the method of providing the sequence of views on the 3D model apply to the method of operating the surgical information system in a same or similar way and shall therefore not be repeated.

Further characteristics of the subject application will become apparent from the description of the embodiments together with the claims and the included drawings. Embodiments according to the subject application can fulfill individual characteristics or a combination of several characteristics.

BRIEF DESCRIPTION OF DRAWINGS

Exemplary embodiments will be described below, without restricting the general intent of the invention, wherein reference is made expressly to the drawings with regard to the disclosure of all details that are not explained in greater detail in the text. The drawings show in.

In the drawings, the same or similar types of elements or respectively corresponding parts are provided with the same reference numbers in order to prevent the item from needing to be reintroduced.

DETAILED DESCRIPTION

Figure 1:
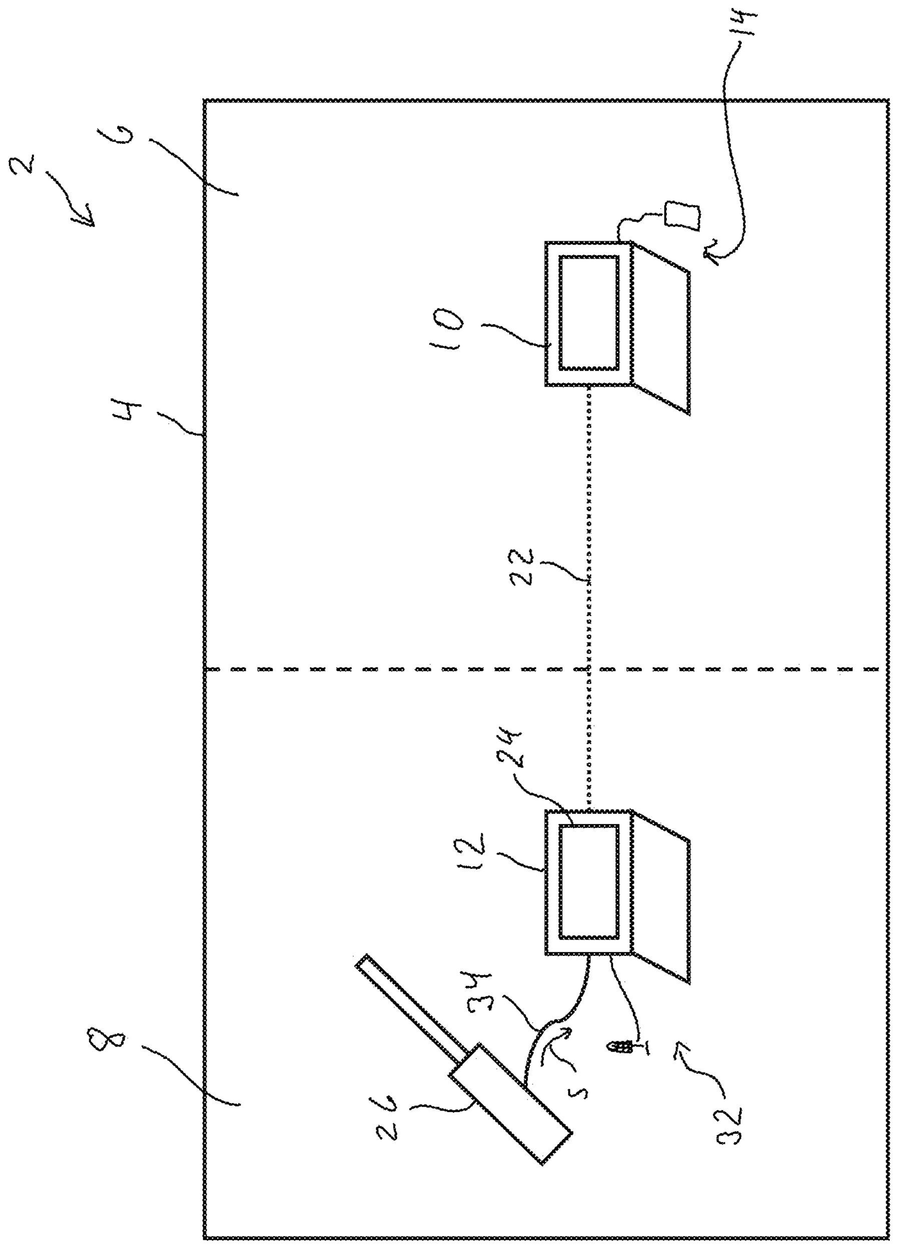
FIG. 1 a simplified surgical information system.

FIG. 1 is a simplified surgical information system 2, which is configured for providing of a sequence of views on and the 3D model of a body part in a surgical environment 4. The surgical environment 4 comprises a working area 6, which is for example an office space. Furthermore, the surgical environment 4 comprises a clean area 8, which is for example an operation room. The surgical information system 2 comprises a first processing device 10, which is located in the working area 6, and a second processing device 12, which is located in the clean area 8. The first processing device 10 and the second processing device 12 are for example computers.

The first processing device 10 is configured to provide a 3D model of the body part, which will be explained in further detail when making reference to FIG. 4. The 3D model can be stored on a non-transitory memory of the first processing device 10 or it can be downloaded via a network. The first processing device 10 is further configured to reproduce the 3D model, for example on a screen. The first processing device 10 is also configured to receive instructions via a user interface 14. The user interface comprises for example a keyboard and a mouse pointer as input devices and a display of the first processing device 10 as an output device. The received instructions define a sequence of views on the 3D model, in that every view defines an orientation of the 3D model and the sequence of views defines a chronological order of views on the 3D model. In order to allow the user to select the desired view, the first processing device 10 provides the user with a functionality to manipulate the 3D model. For example, the user can tilt, rotate and shift the 3D model, and can zoom in and out to magnify or minimize the reproduction of the 3D model.

Figure 4:
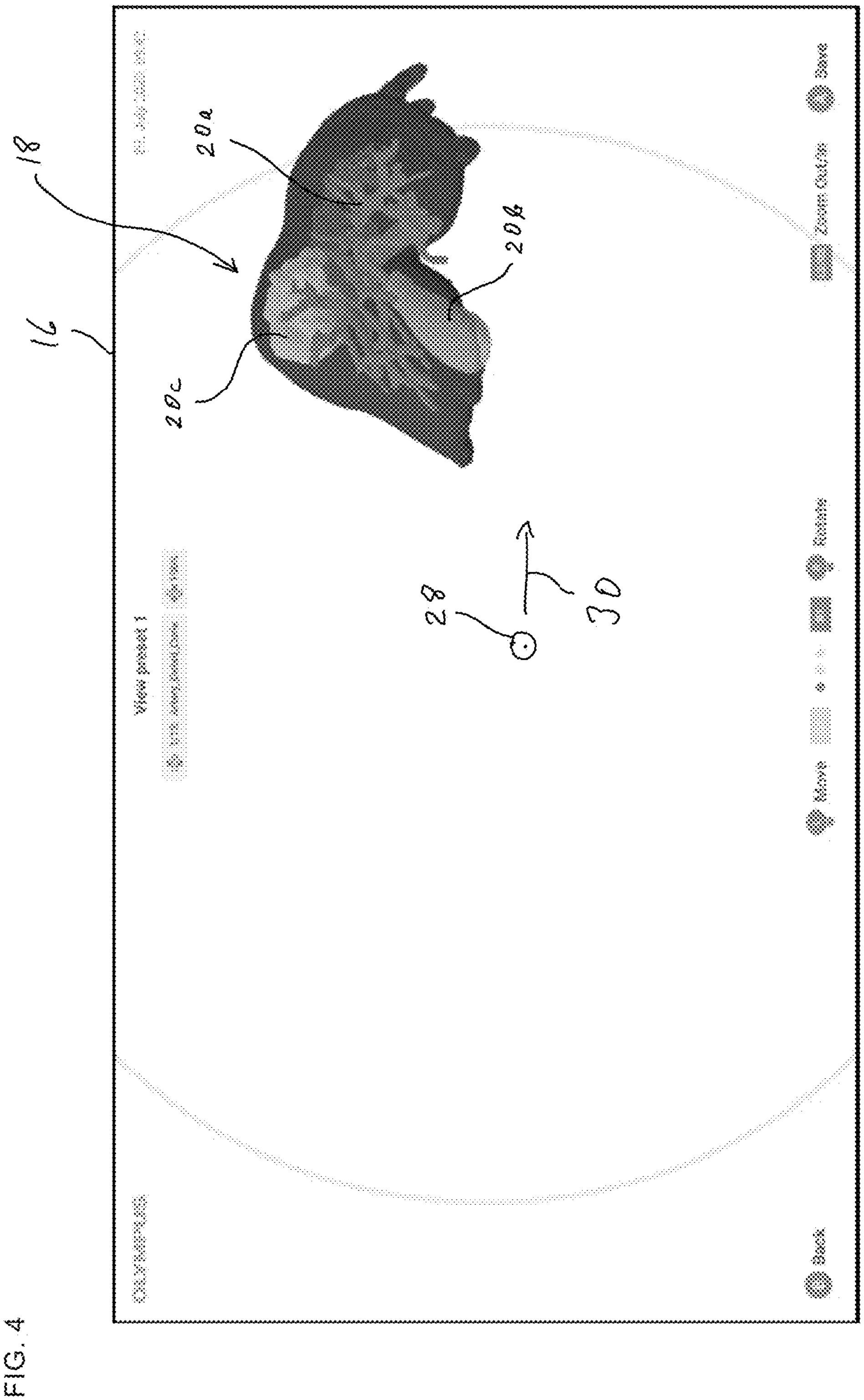

FIG. 4 illustrates an example of view 16 on a 3D model 18 of the body part, which is for example the liver. The 3D model 18 of the body part comprises various sub-parts 20*a*, 20*b*, 20*c*, which are for example veins or arteries (20*a*), channels of the organ (20*b*) or malicious tissue (20*c*). The view 16 defines an orientation of the 3D model 18 in space, which is for example defined using a Cartesian coordinate system. The sequence of views 16, which is input by a user via the user interface 14 of the first processing device 10 not only defines an orientation of the 3D model 18 per view 16 but also defines a sequence of the views 16. This sequence of views 16 places the views 16 in chronological order. The chronological order of the views 16 defines a procedural planning of for example a surgical treatment, which is performed on the body part, that is illustrated in the 3D model 18. The sequence of views 16 is stored together with the 3D model 18, for example on a non-transitory storage medium of the first processing device 10.

Subsequently, the sequence of views 16 together with the 3D model 18 are transmitted or communicated from the first processing device 10 to the second processing device 12. For the data communication, the first processing device 10 and the second processing device 12 are coupled via a data link 22, which can be implemented as a wired or a wireless datalink.

The second processing device 12 is located in the clean area 8. The data communication via the data link 22 advantageously prevents the user of the surgical information system 2 from taking any item from the working area 6 to the clean area 8. This advantageously enhances the hygienic level of the surgical information system 2.

The second processing device 12 is configured to reproduce the sequence of views 16 on a displaying device 24, which forms part of the second processing device 12. For example, the displaying device 24 is a display of the second processing device 12, which can be a computer. By way of an example, the reproduction of the sequence of views 16 serves as a procedural planning for an operator of the surgical instrument 26. The sequence of views 16 can guide the operator or surgeon through a surgical procedure.

As already mentioned before, the 3D model 18 comprises a plurality of sub-parts 20*a*, 20*b*, 20*c* forming the body part, which is illustrated in the 3D model 18. The instructions, which are received via the user interface 14 and the first processing device 10 can further comprise instructions on a transparency value of at least one of the sub-parts 20*a*, 20*b* and/or 20*c* of the body part. There transparency value can for example define an opacity of the sub-parts 20*a*, 20*b*, 20*c* in the view 16 on the 3D model 18. Reducing the opacity of at least one of the subparts 20*a*, 20*b*, 20*c* allows a user to identify structures in parts which are otherwise covered by sub-parts lying in front. However, precise knowledge of the structure of all the subparts 20*a*, 20*b*, 20*c* can be a crucial factor for success of a surgical treatment.

The first processing device 10 can be further configured to additionally store the transparency values of the at least one sub-part 20*a*, 20*b*, 20*c* in the sequence of views 16. The transparency values can be defined for every individual view 16. The information is stored together with the sequence of views 16 and is communicated to the second processing device 12, for display on the displaying device 24 thereof.

The first processing device 10 can be further configured to provide a plurality of virtual camera positions, each defining a direction of view on the 3D model 18. Ba way of an example, a first direction of view 28 can be oriented perpendicular to the drawing plane. An alternative virtual camera position and can define a second direction of view 30, which is for example oriented in the drawing plane. The instructions received at the first processing device 10 comprise instructions on the selected virtual camera position, wherein the virtual camera position(s) can be defined for every view 16. In other words, for every view 16 of the sequence of views 16, a number of individual virtual camera positions can be defined. The virtual camera position is additionally stored together with the sequence of views 16. The virtual camera positions are communicated together with the sequence of views 16 from the first processing device 10 to the second processing device 12 for display on the displaying device 24 of the second processing device 12.

The second processing device 12 can be configured to receive instructions, which are indicative of a selected virtual camera. These instructions can be received via a user interface 32 of the second processing device 12. For example, the user interface 32 can be a keyboard or microphone. The second processing device 12 can be configured to perform speech recognition to capture the instructions that are indicative of the selected virtual camera. The user of the second processing device 12 can select a suitable view from the plurality of virtual camera positions.

The definition of the virtual camera positions can comprise the definition of a default virtual camera position. This is for example the virtual camera position defined by the first direction of view 28 illustrated in FIG. 4. Upon reception of a corresponding command by the user interface 32 at the second processing device 12, the reproduction of the sequence of views 16 switches to the default virtual camera position. This may allow a user of the surgical information system 2 to regain orientation, if necessary.

Figure 3:
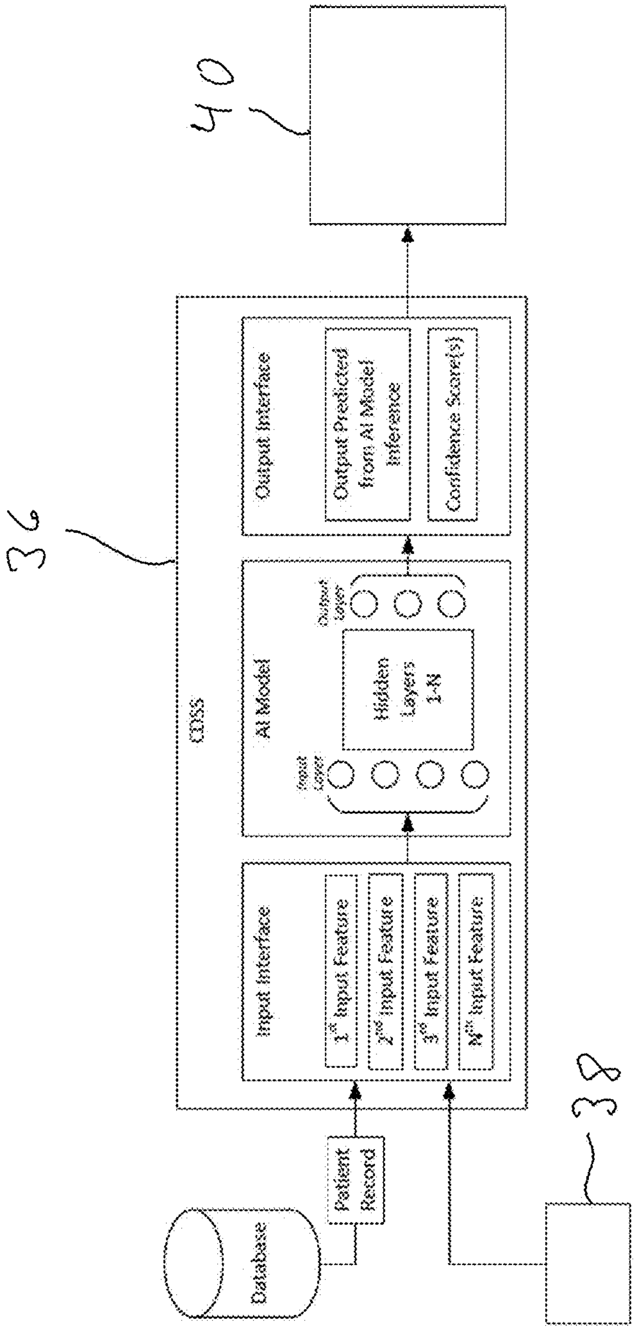

FIG. 3 illustrates a schematic drawing of the computer-based clinical decision support system (CDSS), which by way of an example, is implemented in the first processing device 10. The CDSS implements an artificial intelligence model (AI model). The AI model receives a number of input features via an input interface. The input features are fed to an input layer of the AI model. The AI model performs an interference operation on the input features and provides an output at an output layer. This results in an output at an output interface. The output is also assigned a confidence score. The CDSS is configured to receive inter alia patient data from a patient record as an input feature. The patient data can be stored in a database. Another input features can be instrument data, which are for example data on operating parameters of the surgical instrument 26. This can be live (time dependent) operating parameters or static parameters. Another input feature can be data relative to preferences of a surgeon or operator of the surgical instrument 26. Other data related to preferences of the operator can be related to the reproduction of the views on the displaying device 24. Based on these input features, the CDSS performs a classification of views 16. For this purpose, the CDSS can be aware of all possible views and/or virtual camera positions. This is illustrated in FIG. 3 by the dataset referred to as the sum of views 38. Based on the input features, the CDSS can perform a preselection of views 16 as output data. This is illustrated by the preselected dataset of views 40. Based on the preselected views, a user can further select the desired views 16 at the user interface 14 of the first processing device 10. General and more detailed information on the CDSS will be provided at the end of this description.

Many surgical procedures include milestones, at which surgical standard procedures are performed. The first processing device 10 is configured to receive instructions, which comprise information on a selection of at least one view 16 as a milestone-view. At which view 16 the milestone is reached, is defined during the planning of the procedure. If the milestone-view is displayed in the sequence of views 16, the user of the surgical information system 2 is prompted to the fact, a certain milestone has been reached in the surgical procedure.

It is illustrated in FIG. 1 that the surgical instrument 26 is linked to the second processing device 12 via a data line 34. This data line 34 can be implemented as a wired connection or a wireless connection. The second processing device 12 is configured to receive a signal S from the surgical instrument 26 via the data line 34. This signal S is indicative of a milestone action or a milestone use of the surgical instrument 26. For example, this trigger signal S can be generated at the surgical instrument 26 when a HF-generator (not displayed) is operated. In many surgical procedures, the use of the HF-generator indicates the termination of a certain procedure, which means that a milestone in the surgical procedure has been reached. The trigger signal S triggers the selection of the milestone-view at the second processing device 12.

Figure 2:
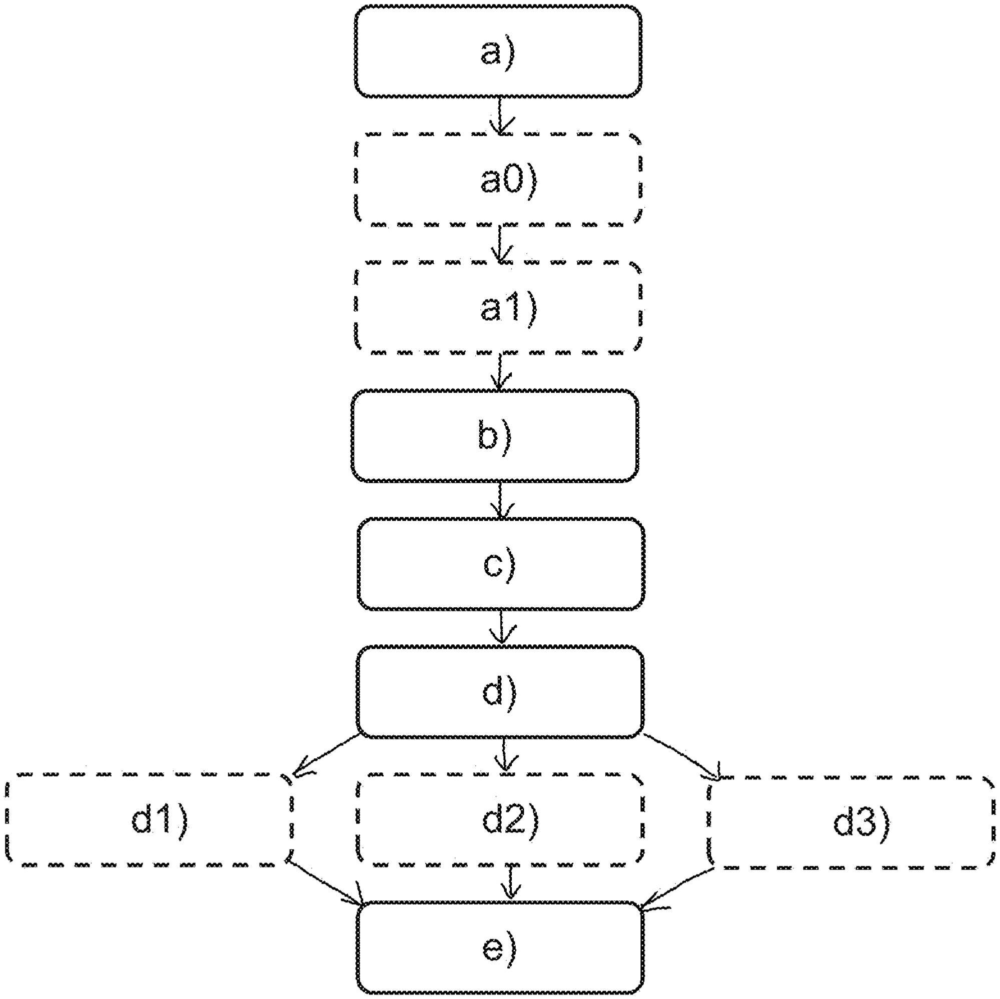
FIG. 2 a flowchart illustrating a method of providing a sequence of views on a 3D model of a body part in a surgical environment, FIG. 3 schematically illustrates a computer-based clinical decision support system (CDSS), which can be implemented in the first processing device and FIG. 4 an exemplary view on a 3D model of a body part.

FIG. 2 illustrates a flowchart of a method of providing a sequence of views 16 on the 3D model 18 of the body part in the surgical environment 4. The surgical environment 4 is illustrated and explained above. The method comprises the steps a), b), c), d), and e). In step a), a 3D model 18 of the body part is provided on the first processing device 10, which is located in the working area 6. In step b), instructions are received at the first processing device 10, wherein the instructions define the sequence of views 16 on the 3D model 18 in that every view 16 defines an orientation of the 3D model 18. The sequence further defines a chronological order of the views 16. In step c), the sequence of views 16 is stored together with the 3D model 18. In step d), the sequence of views 16 is transmitted together with the 3D model 18 to the second processing device 12, which is located in the clean area 8. In step e), the sequence of views 16 is reproduced on the displaying device 24 of the second processing device 12.

The steps shown in dashed line are optional steps of the method. Step a0) relates to performing of a classification of views using the computer-based clinical decision support system. Step a1) refers to the selection of virtual camera views and corresponds to step d1), referring to the display of the view from the selected viewing direction of the virtual camera.

The steps d1), d2), and d3) are not necessarily performed in the named order. They can be performed as alternative steps or in arbitrary order. Step d2) refers to the selection of a default virtual camera view. Step d3) refers to displaying of a view relating to a milestone. This can triggered by signal S.

In the following, general and more detailed information on the implementation of the CDSS (see FIG. 3) will be provided.

FIG. 3 shows a schematic diagram of the exemplary computer-based clinical decision support system (CDSS) that is configured to provide a preselection of views based on input data, which can be patient data, instrument data and/or data relative to preferences of a surgeon. In various embodiments, the CDSS includes an input interface through which the input data, which is for example specific to a patient, is provided as one of the input features to the artificial intelligence (AI) model. The AI model is run on a processor 36, which performs an inference operation in which the input data, for example patient data, instrument data and/or data relative to preferences of a surgeon, are applied to the AI model to generate the preselection of views. The preselected dataset of views 40 can be output through an output interface, which can be the user interface 14 of the first processing device 10. The system output is communicated to a user, e.g., a clinician.

In some embodiments, the input interface may be a direct data link between the CDSS and one or more medical devices, for example the surgical instrument 26 that generates at least some of the input features. For example, the input interface may transmit the input data directly to the CDSS during a therapeutic and/or diagnostic medical procedure. Additionally, or alternatively, the input interface may be a classical user interface that facilitates interaction between a user and the CDSS. For example, the input interface may facilitate a user interface through which the user may manually enter input data like surgeons preferences. The input interface can be the user interface 14 of the first processing device 10. Additionally, or alternatively, the input interface may provide the CDSS with access to an electronic patient record from which one or more input features may be extracted. In any of these cases, the input interface is configured to collect one or more of the input data related features in association with a specific patient on or before a time at which the CDSS is used to assess the selection of views for providing of a procedure planning.

Based on one or more of the input features, the processor 36 performs an inference operation using the AI model to generate the preselection of views. For example, input interface may deliver the input data into an input layer of the AI model which propagates the data as input features through the AI model to an output layer. The AI model can provide a computer system the ability to perform tasks, without explicitly being programmed, by making inferences based on patterns found in the analysis of data. AI model explores the study and construction of algorithms (e.g., machine learning algorithms) that may learn from existing data and make predictions about new data. Such algorithms operate by building an AI model from example training data in order to make data-driven predictions or decisions expressed as outputs or assessments.

There are two common modes for machine learning (ML): supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled, and allowing the algorithm to act on that information without guidance. Unsupervised ML is useful in exploratory analysis because it can automatically identify structure in data.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model may be trained continuously or periodically prior to performance of the inference operation by the processor 36. Then, during the inference operation, the patient specific input features provided to the AI model may be propagated from an input layer, through one or more hidden layers, and ultimately to an output layer that corresponds to the selection of views.

During and/or subsequent to the inference operation, the selection of views may be communicated to the user via the user interface (UI) and/or automatically cause the first processing device 10 to display the preselected views Embodiments according to the invention can be fulfilled through individual characteristics or a combination of several characteristics.

LIST OF REFERENCES

2 surgical information system
4 surgical environment
6 working area
8 clean area
10 first processing device
12 second processing device
14 user interface (first processing device)
16 view
18 3D model
20*a*, 20*b*, 20*c* sub-part
22 data link
24 displaying device
26 surgical instrument
28 first direction of view
30 second direction of view
32 user interface (second processing device)
34 data line
36 processor
38 sum of views
40 preselected dataset of views
S signal
CDSS computer-based clinical decision support system
AI model artificial intelligence model

The invention claimed is:

1. A surgical information system for providing a sequence of views on a 3D model of a body part in a surgical environment, the surgical environment having a working area and a clean area, the surgical information system comprising:
- a first processing device located in the working area; and
- a second processing device located in the clean area,
- wherein the first processing device is configured to:
  - provide and reproduce the 3D model of the body part;
  - receive instructions defining a sequence of views on the 3D model in that every view defines an orientation of the 3D model and the sequence defines a chronological order of the views on the 3D model;
  - store the sequence of views together with the 3D model; and
  - transmit the sequence of views and the 3D model to the second processing device located in the clean area, and
- wherein the second processing device is configured to reproduce the sequence of views transmitted by the first processing device on a displaying device.

2. The surgical information system according to claim 1,
- wherein the 3D model comprises a plurality of sub-parts forming the body part and the instructions received comprise instructions on a transparency value of at least one sub-part of the plurality of sub-parts,
- wherein the first processing device is further configured to additionally store the transparency value of the at least one sub-part in the sequence of views, and
- wherein the second processing device is further configured to reproduce the sequence of views according to the transparency value stored in the sequence of views.

3. The surgical information system according to claim 1, wherein the first processing device is further configured to:

provide a plurality of virtual camera positions each defining a direction of view on the 3D model; and receive the instructions which further defines at least one selected virtual camera position of the plurality of virtual camera positions; and additionally store the at least one selected virtual camera position in the sequence of views, and wherein the second processing device is further configured to:

receive the instructions indicative of the at least one selected virtual camera position; and reproduce the sequence of views from the one or more direction of views on the 3D model as defined by the at least one selected virtual camera position.

4. The surgical information system according to claim 3, wherein the instructions which further define the at least one selected virtual camera position comprise a selection of a default virtual camera position, wherein the first processing device is further configured to additionally store the default virtual camera position in the sequence of views, and wherein the second processing device is further configured to:

receive the instructions indicative of the selection of the default virtual camera position; and reproduce at least one view of the sequence of views from the direction of view on the 3D model as defined by the selected default virtual camera position.

5. The surgical information system according to claim 1, wherein the first processing device is further configured to:

receive input data indicative of patient data, instrument data and/or data relating to preferences of a surgeon; and perform a classification of views based on the received input data using a computer-based clinical decision support system (CDSS) implemented in the first processing device, and wherein in performing the classification of views, the first processing device is configured to:

receive a plurality of views through an input interface of the CDSS as an input feature of an artificial intelligence (AI) model;

perform an inference operation, in which the plurality of views is applied to the AI model to generate the classification of views; and communicate the classification of views through a user interface (UI) as a preselection of views, based on which the definition of the sequence of views on the 3D model is performed.

6. The surgical information system according to claim 1; wherein the first processing device is further configured to:

receive the instructions further defining a selection of at least one milestone-view in the sequence of views; and additionally store the at least one milestone-view in the sequence of views together with the 3D model, and wherein the second processing device is further configured to:

receive instructions indicative of a selection of a milestone-view of the at least one milestone-view and to reproduce the selected milestone-view.

7. The surgical information system according to claim 6, wherein the second processing device is further configured to receive a signal from a surgical instrument coupled to the second processing device, the signal being indicative of a milestone action or use of the surgical instrument, and wherein the signal triggers the selection of the at least one milestone-view as the instruction further defining the selection of the milestone-view.

8. A method of providing a sequence of views on a 3D model of a body part in a surgical environment, the surgical environment having a working area and a clean area, the method comprising:

by a first processing device located in the working area:

providing and reproducing the 3D model of the body part;

receiving instructions defining a sequence of views on the 3D model in that every view defines an orientation of the 3D model and the sequence defines a chronological order of the views on the 3D model;

storing the sequence of views together with the 3D model; and transmitting the sequence of views and the 3D model to a second processing device located in the clean area; and by the second processing device, reproducing the sequence of views transmitted by the first processing device on a displaying device.

9. The method according to claim 8, wherein the 3D model comprises a plurality of sub-parts forming the body part and the instructions received comprise instructions on a transparency value of at least one sub-part of the plurality of sub-parts, and wherein the method comprises:

by the first processing device, additionally storing the transparency value of the at least one sub-part in the sequence of views; and by the second processing device, reproducing the sequence of views according to the transparency value stored in the sequence of views.

10. The method according to claim 8, further comprising:

by the first processing device:

providing a plurality of virtual camera positions each defining a direction of view on the 3D model, receiving the instructions which further defines at least one selected virtual camera position of the plurality of virtual camera positions; and additionally storing the at least one selected virtual camera position in the sequence of views, by the second processing device:

receiving the instructions indicative of the at least one selected virtual camera position; and reproducing the sequence of views from the one or more direction of view on the 3D model as defined by the at least one selected virtual camera position.

11. The method according to claim 10, wherein the instructions which further define the at least one selected virtual camera position comprise a selection of a default virtual camera position, and wherein the method further comprises:

by the first processing device, additionally storing the default virtual camera position in the sequence of views, and by the second processing device:

receiving the instruction indicative of the selection of the default virtual camera position; and reproducing at least one view of the sequence of views from the direction of view on the 3D model as defined by the selected default virtual camera.

12. The method according to claim 8, further comprising: by the first processing device, receiving input data indicative of patient data, instrument data and/or data relating to preferences of a surgeon; and performing a classification of views based on the received input data using a computer-based clinical decision support system (CDSS) implemented in the first processing device, wherein performing the classification of views comprises:

receiving a plurality of views through an input interface of the CDSS as an input feature of an artificial intelligence (AI) model;

performing an inference operation, in which the plurality of views is applied to the AI model to generate the classification of views; and communicating the classification of views through a user interface (UI) as a preselection of views, based on which the definition of the sequence of views on the 3D model is performed.

13. The method according to claim 8, further comprising: by the first processing device:

receiving the instructions further defining a selection of at least one milestone-view in the sequence of views; and additionally storing the at least one milestone-view in the sequence of views together with the 3D model; and by the second processing device receiving instructions indicative of the selection of the milestone-view of the at least one milestone-view and reproducing the selected milestone-view.

14. The method according to claim 13, further comprising:

by the second processing device, receiving of a signal from a surgical instrument coupled to the second processing device, the signal being indicative of a milestone action or use of the surgical instrument, wherein the signal triggers the selection of the at least one milestone-view as the instruction further defining the selection of the milestone-view.

15. One or more non-transitory computer-readable storage mediums storing instructions that cause a computer of a first processing device and a computer of a second processing device of a surgical information system to providing a sequence of views on a 3D model of a body part in a surgical environment, the surgical environment having a working area and a clean area, wherein the instructions, when executed, cause the computer of the first processing device to at least perform:

providing and reproducing the 3D model of the body part;

receiving instructions defining a sequence of views on the 3D model in that every view defines an orientation of the 3D model and the sequence defines a chronological order of the views on the 3D model;

storing the sequence of views together with the 3D model; and transmitting the sequence of views and the 3D model to the second processing device located in the clean area, and wherein the instructions, when executed, cause the computer of the second processing device to at least perform reproduce the sequence of views transmitted by the first processing device on a displaying device.

16. The one or more non-transitory computer-readable storage mediums according to claim 15, wherein the 3D model comprises a plurality of sub-parts forming the body part and the instructions received comprise instructions on a transparency value of at least one sub-part of the plurality of sub-parts, wherein the instructions, when executed, cause the computer of the first processing device to perform additionally storing the transparency value of the at least one sub-part in the sequence of views, and wherein the instructions, when executed, cause the computer of the second processing device to perform reproducing the sequence of views according to the transparency value stored in the sequence of views.

17. The one or more non-transitory computer-readable storage mediums according to claim 15, wherein the instructions, when executed, cause the computer of the first processing device to perform:

providing a plurality of virtual camera positions each defining a direction of view on the 3D model; and receiving the instructions which further defines at least one selected virtual camera position of the plurality of virtual camera positions; and additionally storing the at least one selected virtual camera position in the sequence of views, and wherein the instructions, when executed, cause the computer of the second processing device to perform:

receiving the instructions indicative of the at least one selected virtual camera position; and reproducing the sequence of views from the one or more direction of views on the 3D model as defined by the at least one selected virtual camera position.

18. The one or more non-transitory computer-readable storage mediums according to claim 17, wherein the instructions which further define the at least one selected virtual camera position comprise a selection of a default virtual camera position, wherein the instructions, when executed, cause the computer of the first processing device to perform additionally storing the default virtual camera position in the sequence of views, and wherein the instructions, when executed, cause the computer of the second processing device to perform:

receiving the instructions indicative of the selection of the default virtual camera position; and reproducing at least one view of the sequence of views from the direction of view on the 3D model as defined by the selected default virtual camera position.

19. The one or more non-transitory computer-readable storage mediums according to claim 15, wherein the instructions, when executed, cause the computer of the first processing device to perform:

receiving input data indicative of patient data, instrument data and/or data relating to preferences of a surgeon; and performing a classification of views based on the received input data using a computer-based clinical decision support system (CDSS) implemented in the first processing device, and wherein performing the classification of views comprises:

receiving a plurality of views through an input interface of the CDSS as an input feature of an artificial intelligence (AI) model;

performing an inference operation, in which the plurality of views is applied to the AI model to generate the classification of views; and communicating the classification of views through a user interface (UI) as a preselection of views, based on which the definition of the sequence of views on the 3D model is performed.

20. The one or more non-transitory computer-readable storage mediums according to claim 15, wherein the instructions, when executed, cause the computer of the first processing device to perform:

receiving the instructions further defining a selection of at least one milestone-view in the sequence of views; and additionally storing the at least one milestone-view in the sequence of views together with the 3D model, and wherein the instructions, when executed, cause the computer of the second processing device to perform:

receiving instructions indicative of a selection of a milestone-view of the at least one milestone-view and reproducing the selected milestone-view; and receiving a signal from a surgical instrument coupled to the second processing device, the signal being indicative of a milestone action or use of the surgical instrument, wherein the signal triggers the selection of the at least one milestone-view as the instruction further defining the selection of the milestone-view.

* * * * *